(12) United States Patent
Blin et al.

(10) Patent No.: US 9,320,693 B2
(45) Date of Patent: Apr. 26, 2016

(54) COSMETIC COMPOSITION WITH A VOLUMIZING EFFECT

(75) Inventors: Xavier Blin, Paris (FR); Claudia Barba, Paris (FR)

(73) Assignee: L'OREAL, Paris (FR)

( * ) Notice: Subject to any disclaimer, the term of this patent is extended or adjusted under 35 U.S.C. 154(b) by 1731 days.

(21) Appl. No.: 11/641,785

(22) Filed: Dec. 20, 2006

(65) Prior Publication Data

US 2007/0141003 A1 Jun. 21, 2007

Related U.S. Application Data

(60) Provisional application No. 60/757,850, filed on Jan. 11, 2006.

(30) Foreign Application Priority Data

Dec. 21, 2005 (FR) ..................... 05 13075

(51) Int. Cl.
| | |
|---|---|
| *A61K 8/37* | (2006.01) |
| *A61K 8/34* | (2006.01) |
| *A61Q 1/02* | (2006.01) |
| *A61Q 1/06* | (2006.01) |
| *A61Q 1/12* | (2006.01) |
| *A61Q 19/00* | (2006.01) |

(52) U.S. Cl.
CPC ............... *A61K 8/345* (2013.01); *A61K 8/375* (2013.01); *A61Q 1/02* (2013.01); *A61Q 1/06* (2013.01); *A61Q 1/12* (2013.01); *A61Q 19/001* (2013.01)

(58) Field of Classification Search
CPC ......... A61Q 15/00; A61Q 19/00; A61Q 1/06; A61Q 17/04; A61Q 1/02; A61Q 1/08; A61Q 1/10; A61Q 17/005; A61Q 17/02; A61Q 19/005; A61Q 19/02; A61Q 19/06; A61Q 19/08; A61Q 1/04; A61Q 5/00; A61Q 5/12
See application file for complete search history.

(56) References Cited

U.S. PATENT DOCUMENTS

| | | | |
|---|---|---|---|
| 4,002,775 A | | 1/1977 | Kabara |
| 4,335,104 A | * | 6/1982 | VanCleave ............ 424/59 |
| 4,659,562 A | | 4/1987 | Arraudeau et al. |
| 4,820,510 A | | 4/1989 | Arraudeau et al. |
| 5,690,919 A | | 11/1997 | Röckl et al. |
| 5,874,069 A | | 2/1999 | Mendolia et al. |
| 5,919,441 A | | 7/1999 | Mendolia et al. |
| 5,981,680 A | | 11/1999 | Petroff et al. |
| 6,051,216 A | | 4/2000 | Barr et al. |
| 6,358,498 B1 | * | 3/2002 | Yu et al. ............ 424/64 |
| 2002/0002793 A1 | * | 1/2002 | Krull et al. ............ 44/388 |
| 2002/0039561 A1 | * | 4/2002 | Doughty et al. ........ 424/59 |
| 2005/0026795 A1 | * | 2/2005 | Filippi ............ 510/130 |
| 2005/0244355 A1 | * | 11/2005 | Sabino et al. ........ 424/70.1 |
| 2006/0153792 A1 | | 7/2006 | Arnaud et al. |

FOREIGN PATENT DOCUMENTS

| | | | | |
|---|---|---|---|---|
| DE | 195 41 967 A1 | | 5/1997 | |
| EP | 0 667 146 A1 | | 8/1995 | |
| EP | 0 847 752 A1 | | 6/1998 | |
| FR | WO 98/22075 | * | 5/1998 | |
| FR | WO98/22075 | * | 5/1998 | ........ 424/401 |
| FR | 2 842 417 | | 1/2004 | |
| WO | WO 2004/030605 A2 | | 4/2004 | |

* cited by examiner

*Primary Examiner* — Audrea Buckley
(74) *Attorney, Agent, or Firm* — Oliff PLC

(57) ABSTRACT

The present invention relates to the cosmetic use of at least one $C_4$-$C_{16}$ glycol with a hydrocarbon-chain and/or of a hydroxylated ester resulting from the esterification of polyol and/or of $C_4$-$C_{16}$ carboxylic acid(s), in a composition for caring for and/or making up the skin and/or the lips, as an agent for reinforcing the natural flesh tint of the skin and/or the lips and/or the natural volume of the lips.

41 Claims, No Drawings

COSMETIC COMPOSITION WITH A VOLUMIZING EFFECT

This non provisional application claims the benefit of French Application No. 05 13075 filed on Dec. 21, 2005 and U.S. Provisional Application No. 60/757,850 filed on Jan. 11, 2006.

The invention relates to natural makeup for the skin and/or the lips, and is more particularly directed towards reinforcing their natural flesh tint and, as regards the lips, towards giving them a volumized effect.

According to the invention, the term "natural makeup" for the skin means a means for naturally colouring the skin, as opposed to the existing means for artificially colouring the skin using self-tanning agents or melanin synthesis stimulators (pigmentation) and/or makeup agents such as dyes, pigments or specific fillers capable of giving the skin an optical coloration effect.

According to the invention, the term "natural makeup" for the lips means a means for naturally colouring the lips and/or making them look fleshy, as opposed to conventional lip makeup that uses only makeup agents such as dyes, specific pigments or reflective particles capable of giving the lips an optical coloration and/or volume effect (pouty effect).

According to the invention, the term "naturally colour" means stimulating the naturally pinkish coloration of the skin and/or the lips.

According to the invention, the term "making fleshy" means increasing the size and/or volume and/or thickness of the lips and/or remodelling them and/or making them smooth and/or giving them a more swollen or fleshy appearance.

As regards the latter effect, it is quite clear that it is a constant demand of a large number of consumers, who do not hesitate in certain cases in resorting to cosmetic surgery to obtain such an effect, which then becomes permanent. However, this irreversibility, associated with the increased risk of toxicity and/or allergy due to the invasive nature of the corresponding intervention, may moreover be of a dissuasive nature as regards other potential consumers.

Conventional makeup, which is more accessible and non-invasive, makes it possible to mimic this effect by acting especially on optical phenomena that consist in creating localized gloss in well-defined regions of the lips, or else by superposing two types of gloss, of point and diffuse type, in order to generate an optical illusion and thus create a sensation of volume. However, this alternative is a virtual effect, which is occasionally not perceptible to the consumer.

One of the aspects of the present invention is directed, precisely, towards obtaining cosmetic compositions that are capable of affording a real "pouty" effect in terms of size and/or volume of the lips.

Consequently, according to one of its aspects, the invention relates to the cosmetic use of at least one glycol with a $C_4$-$C_{16}$ hydrocarbon-based chain and/or of a hydroxylated ester resulting from the esterification of polyol and of $C_4$-$C_{16}$ carboxylic acid(s), in a composition for caring for and/or making up the skin and/or the lips, as an agent for reinforcing the natural flesh tint of the skin and/or of the lips and/or the natural volume of the lips.

According to another aspects, the invention relates to a cosmetic method comprising at least the step of using at least one glycol with a $C_4$-$C_{16}$ hydrocarbon-based chain and/or of a hydroxylated ester resulting from the esterification of polyol and of $C_4$-$C_{16}$ carboxylic acid(s), in a composition for caring for and/or making up the skin and/or the lips, as an agent for reinforcing the natural flesh tint of the skin and/or of the lips and/or the natural volume of the lips.

According to one particular embodiment, the said agent is a hydroxylated ester resulting from the esterification of polyol and of $C_4$-$C_{16}$ carboxylic acid(s).

According to another particular embodiment, the said agent is a glycol with a $C_6$-$C_{14}$ hydrocarbon-based chain.

According to yet another particular embodiment, the said agent is a glycol with a $C_4$-$C_{16}$ hydrocarbon-based chain and a hydroxylated ester resulting from the esterification of polyol and of $C_4$-$C_{16}$ carboxylic acid.

According to an embodiment, the instant invention relates to a cosmetic composition intended for the making up of the skin and/or the lips comprising in a physiologically acceptable medium, less than 5 ù by weight of water and at least one glycol with a $C_4$-$C_{16}$ hydrocarbon-based chain and/or a hydroxylated ester of polyol and of $C_4$-$C_{16}$ carboxylic acid(s).

The term "cosmetic use" means a non-therapeutic use capable of producing an effect without, however, preventing or correcting a dysfunction of keratin materials.

The term "cosmetic use" also means a use of a composition containing physiologically acceptable ingredients.

The term "cosmetic method" means a non-therapeutic method capable of producing an effect without, however, preventing or correcting a dysfunction of keratin materials. The term "cosmetic method" also means a non-therapeutic method comprising at least the step of using at least one composition containing physiologically acceptable ingredients.

According to another of its aspects, the present invention is also directed towards cosmetic compositions for caring for and/or making up the skin and/or the lips, containing, in a physiologically acceptable medium, at least:
  one dyestuff, and
  one glycol with a $C_4$-$C_{16}$ hydrocarbon-based chain or a hydroxylated ester of polyol and of $C_4$-$C_{16}$ carboxylic acid(s).

According to an embodiment, the present invention relates to a cosmetic composition for making up the skin and/or the lips comprising in a physiologically acceptable medium at least:
  one dyestuff, and
  one glycol with a $C_5$-$C_7$ or $C_9$-$C_{16}$ hydrocarbon-based chain and/or a hydroxylated ester of polyol and of $C_4$-$C_{16}$ carboxylic acid(s).

According to another embodiment, the present invention relates to a cosmetic composition for caring for the skin and/or the lips containing in a physiologically acceptable medium at least:
  one dyestuff, and
  one glycol with a $C_5$-$C_7$ or $C_9$-$C_{16}$ hydrocarbon-based chain and/or a hydroxylated ester of polyol and of $C_4$-$C_{11}$ or $C_{13}$-$C_{16}$ carboxylic acid(s).

According to another of its aspects, the invention relates to cosmetic compositions for caring for and/or making up the skin and/or the lips, containing, in a physiologically acceptable medium:
  at least one glycol with a $C_4$-$C_{16}$ hydrocarbon-based chain and/or a hydroxylated ester of polyol and of $C_4$-$C_{16}$ carboxylic acid(s), and
  less than 5% by weight of water relative to its total weight.

The cosmetic compositions according to the invention are more particularly intended for topical application.

Another aspect of the invention relates to a cosmetic method for making up the skin and/or the lips, which is directed towards giving a healthy complexion effect using a composition in accordance with the invention, and also to a process for caring for and/or making up the lips, comprising the application to the lips of a composition that is also in accordance with the present invention.

The compositions according to the invention may also be used to afford a naturally healthy complexion, in particular by application to the face. The compositions may be applied daily to the entire face to obtain a uniform natural complexion.

The application may also be limited to, renewed on or reinforced on the cheeks and the cheekbones, for example to accentuate the "healthy appearance" effect on particular areas of the face.

Thus, the compositions may be in the form of a skincare base, a care cream (day cream, night cream or anti-wrinkle cream), a makeup base or a tinted care cream.

The compositions according to the invention may also be used to hide or fade out skin defects, in particular bags under and/or shadows around the eyes, to obtain a homogeneous, uniform complexion, of lively, light, natural appearance. They may thus make it possible to homogenize and/or clarify the complexion and/or to reduce the hazy complexion effect.

The compositions may also be used to improve the appearance of the lips or the contour of the lips, especially to modify the coloration of the lips or to stimulate their natural coloration, to increase the volume of the lips and/or to model them and/or make them smoother. They may thus be used to make the lips fleshy, especially by increasing the size and/or volume and/or thickness of the lips and/or remodel them and/or make them smooth and/or give them a more swollen or fleshy appearance.

Depending on the sites of application for which they are intended, the compositions may be a natural makeup product for the skin in the form of a skincare base or cream, a makeup base, a tinted cream, a foundation in liquid, semi-solid or powder form, an eye contour care product, a concealing care serum, a concealer stick or a natural makeup product for the lips in the form of a lipstick, a liquid gloss, a lipstick paste, a lip contour pencil, a lipcare balm or a lip varnish, also known as a lip lacquer.

Some of the esters under consideration according to the invention are already known for their antiseptic properties and are conventionally used in this respect in compositions intended to be administered to man or animals as pharmaceutical, nutritional and cosmetic compositions. The presence of these compounds ensures stability over time for the corresponding compositions. Thus, document U.S. Pat. No. 5,690,919 describes deodorants comprising glyceride monocaprylate as antimicrobial agent. Similarly, document DE 195 41 967 describes aqueous solutions comprising these same esters as microbicides. More generally, patent U.S. Pat. No. 4,002,775 proposes the use of monoesters of polyol and a $C_{12}$ aliphatic fatty acid as microbicidal agent in compositions intended for nutritional use.

For its part, the invention results from the demonstration by the inventors that the compounds under consideration according to the invention prove to have, contrary to all expectation, advantageous properties in terms of natural makeup of the skin and/or the lips.

Thus, as more particularly concerns the lips, it has been noted that the placing in contact of the lips with these compounds induces a significant swelling effect capable of affording the desired fleshy effect.

Glycols

The glycol used according to the invention may have a $C_4$-$C_{16}$ hydrocarbon-based chain and for example has a $C_6$-$C_{14}$, $C_7$-$C_{12}$ and for example $C_7$-$C_{10}$ hydrocarbon-based chain.

For example, the glycol used according to the invention may have a $C_5$-$C_7$ or $C_9$-$C_{16}$, $C_6$-$C_7$ or $C_{10}$-$C_{16}$ hydrocarbon-based chain. In one embodiment, in which the glycol is used without polyol ester, it for example a glycol with a $C_6$-$C_{14}$ hydrocarbon-based chain.

The term "glycol with a $C_x$ hydrocarbon-based chain" is intended to denote the compounds of formula (I):

in which R is a $C_{x-2}$ alkyl radical.

The glycol with a hydrocarbon-based chain may have a $C_8$-$C_{10}$ hydrocarbon-based chain.

It may be caprylyl glycol and as example the compound sold under the name Caprylyl Glycol Dermosoft Octiol from Straetmans.

The glycol(s) may be present in these compositions in a content ranging from 0.05% to 20%, for example from 0.1% to 10%, or for example less than 5% by weight, as example from 0.1% to 5% and for instance from 0.5% to 2% by weight relative to the total weight of the composition.

Esters

The esters considered according to the present invention may be hydroxylated esters resulting from the esterification of polyol and of $C_4$-$C_{16}$, for instance $C_6$-$C_{12}$, for instance $C_7$-$C_{10}$ and for instance $C_8$-$C_9$ carboxylic acid(s).

For example, the esters according to the invention may be hydroxylated esters resulting from the esterification of polyol and of $C_4$-$C_{11}$ or $C_{13}$-$C_{16}$, for instance $C_4$-$C_9$, or in $C_{11}$ or in $C_{13}$-$C_{16}$ carboxylic acid(s).

According to an embodiment, the esters suitable for the invention may be hydroxylated esters resulting from the esterification of polyols and of $C_4$-$C_{11}$ or $C_{13}$-$C_{16}$ carboxylic acid(s).

The esters used according to the invention are in a hydroxylated form, i.e. they bear at least one, or two, or three or more, hydroxyl functions, the hydroxylated functions being present on the alcohol residue of the ester.

The esters may be $C_{10}$-$C_{20}$ and may contain at least one fatty chain.

In general, they are derived from the esterification of at least one hydroxyl function of a polyol with a $C_4$-$C_{16}$ carboxylic acid.

According to one embodiment, the esters that are suitable for the present invention may be derived from the esterification of polyol with various carboxylic acids, provided that, of course, the ester thus obtained contains at least one, for example at least two free hydroxyl functions. It may be a hydroxylated monoester, a hydroxylated diester or a mixture thereof.

Polyols

For the purposes of the invention, the term "polyol" means any organic molecule comprising in its chemical structure at least two hydroxyl groups (OH).

The polyol may be a linear, branched or cyclic, saturated or unsaturated hydrocarbon-based compound bearing at least two and in particular at least three OH functions.

The polyol may be a hydrocarbon-based compound bearing at least two carbon atoms and less than 15 carbon atoms, and for instance bearing at least two hydroxyl groups and being for instance from 2 to 10 hydroxyl groups.

According to an embodiment, it is a hydrocarbon-based compound containing from 2 to 12 carbon atoms and for example from 2 to 8 carbon atoms.

The polyol may be a compound containing from 2 to 8 carbon atoms and from 2 to 6 hydroxyl functions, for instance ethylene glycol, glycerol, 1,2,3-trihydroxyhexane, butanediol, 1,2-propanediol, erythritol, arabitol, adonitol or dulcitol, pentanediols an in particular 1,2-pentanediol, and sorbitol, or mixtures thereof.

Glycerol derivatives are, for example, butyl diglycol, polyglyceryl-3 diisostearate and castor oil. The polyol may be chosen from the group consisting of glycerol polymers and copolymers, for instance hexaglycerol and diglycerol.

Glycol derivatives are, for example, ethylene glycol, propylene glycol, hexylene glycol, isoprene glycol, butylene glycol and pentylene glycol, and those defined above.

The polyol may also be chosen from the group consisting of sugars such as glucose, fructose, xylose, trehalose, sucrose, maltose and lactose, and mixtures thereof.

A mixture polyols may also be used.

The polyol used according to the invention may be chosen from the group consisting of glycerol and glycols, and derivatives thereof.

The polyols may be chosen from the group consisting of glycerol and 1,2-propylene glycol, or a mixture of two or more of these polyols.

Carboxylic Acid

The carboxylic acid may be linear or branched, and saturated or unsaturated.

It may be a linear monocarboxylic acid.

As illustrations of monocarboxylic acids that are suitable for the invention, mention may be made of butanoic acid, pentanoic acid, hexanoic acid, heptanoic acid, octanoic acid, nonanoic acid, decanoic acid, undecanoic acid, dodecanoic acid, tridecanoic acid, tetradecanoic acid, heptadecanoic acid, hexadecanoic acid and pentadecanoic acid.

Representative branched acids that may be mentioned include isobutanoic acid, isopentanoic acid, pivalic acid, isohexanoic acid, isoheptanoic acid, isooctanoic acid, dimethyloctanoic acid, isononanoic acid, isodecanoic acid, isoundecanoic acid, isododecanoic acid, isotridecanoic acid, isotetradecanoic acid, isopentadecanoic acid, isohexadecanoic acid, 2-ethylhexanoic acid, 2-butyloctanoic acid and 2-hexyldecanoic acid.

Hydroxy acids such as 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytridecanoic acid, 2-hydroxytetradecanoic acid and 2-hydroxyhexadecanoic acid are also suitable for present invention.

The acid may be a $C_7$-$C_{10}$ non-hydroxylated acid and for example heptanoic acid, caprylic acid or capric acid.

Esters chosen from the group consisting of monoglyceryl and/or diglyceryl caprylates, monoglyceryl and/or diglyceryl heptanoate, propylene glycol caprylate and propylene glycol heptanoate, and mixtures thereof, are suitable for the invention.

The ester may be particularly monoglyceryl caprylate and mixtures thereof.

Mention may be made of the compounds sold under the name Capmul MCM or Akoline MCM (glyceryl caprylate/caprate) from Abitec or Dermosoft GMCY (glyceryl caprylate) from Straetmans, Capmul 708 G (glyceryl caprylate containing 75% monoesters) from Abitec and Capmul 907P (propylene glycol heptanoate) from Abitec, or alternatively Capmul 908P (propylene glycol caprylate) from Abitec.

The ester(s) may be present in these compositions in a content ranging from 0.05% to 20%, for example from 0.1% to 10%, or in less than 5% by weight, for example from 0.2% to 5% and for instance from 0.5% to 2% by weight relative to the total weight of the composition.

The esters may be introduced into the cosmetic compositions in accordance with the present invention according to conventional protocols.

Irrespective of its nature, the agent intended to reinforce the natural flesh tint of the skin and/or of the lips and/or the natural volume of the lips may be present in these compositions in a content ranging from 0.05% to 20%, for example from 0.1% to 10%, or in less than 5% by weight, for example from 0.2% to 5% and for instance from 0.5% to 2% by weight relative to the total weight of the composition.

The composition of the invention may be in solid, pasty or more or less fluid liquid form. It may be a solid or soft anhydrous gel, a liquid oily phase or a mousse.

According to one variant of the invention, the compositions may contain less than 5% by weight, for example less than 3% by weight and for instance less than 1% by weight of water, or are even free of water, i.e. anhydrous.

Solvent Phase

The composition according to the invention may comprise at least one non-aqueous solvent phase.

This phase is capable of forming a continuous film and contains, as its name indicates, at least one non-aqueous organic solvent, which may be a compound that is water-insoluble and liquid at room temperature and atmospheric pressure.

For the purposes of the invention, the term "volatile compound" means any compound (or non-aqueous medium) capable of evaporating on contact with keratin materials or the lips in less than one hour, at room temperature and atmospheric pressure. The volatile compound is a volatile cosmetic compound, which is liquid at room temperature, having a non-zero vapour pressure, at room temperature and atmospheric pressure, having a vapour pressure ranging from 0.13 Pa to 40 000 Pa ($10^{-3}$ to 300 mmHg), for instance ranging from 1.3 Pa to 13 000 Pa (0.01 to 100 mmHg) and for instance ranging from 1.3 Pa to 1300 Pa (0.01 to 10 mmHg).

In contrast, the term "non-volatile compound" means a compound which remains on keratin materials or the lips, at room temperature and atmospheric pressure, for at least several hours and which has a vapour pressure of less than $10^{-3}$ mmHg (0.13 Pa).

The volatile compound that is water-insoluble and liquid at room temperature may be a cosmetically acceptable oil (fatty substance that is liquid at 25° C. and atmospheric pressure) or organic solvent. The term "cosmetically acceptable" means a compound whose use is compatible with application to keratin materials.

The volatile oils may be hydrocarbon-based oils, silicone oils or fluoro oils, or mixtures thereof.

The term "hydrocarbon-based oil" means an oil mainly containing hydrogen and carbon atoms and possibly oxygen, nitrogen, sulfur or phosphorus atoms. The volatile hydrocarbon-based oils may be chosen from the group consisting of hydrocarbon-based oils containing from 8 to 16 carbon atoms, and for instance branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar® or Permethyl®, branched $C_8$-$C_{16}$ esters and isohexyl neopentanoate, and mixtures thereof. Other volatile hydrocarbon-based oils, for instance petroleum distillates, especially those sold under the name Shell Solt® by the company Shell, may also be used.

Volatile oils that may also be used include volatile silicones, for instance volatile linear or cyclic silicone oils, especially those with a viscosity of less than 8 centistokes and for instance containing from 2 to 10 silicon atoms, these silicones optionally comprising alkyl or alkoxy groups containing from 1 to 22 carbon atoms. As volatile silicone oils that may be used in the invention, mention may be made of octamethylcyclotetrasiloxane, decamethylcyclopentasiloxane, dodecamethylcyclo-hexasiloxane, heptamethylhexyltrisiloxane, heptamethyloctyltrisiloxane, hexamethyl-disiloxane, octamethyltrisiloxane, decamethyltetrasiloxane and dodecamethyl-pentasiloxane, and mixtures thereof.

The non-aqueous solvent phase may also comprise at least one non-volatile compound that is water-insoluble and liquid at room temperature, for instance at least one non-volatile oil, which may be chosen from the group consisting of non-volatile and glossy hydrocarbon-based oils and/or silicone oils and/or fluoro oils.

Non-volatile hydrocarbon-based oils that may be mentioned include:
hydrocarbon-based oils of plant origin, such as triesters of fatty acids and of glycerol, the fatty acids of which may have varied chain lengths from $C_4$ to $C_{24}$, these chains possibly being linear or branched, and saturated or unsaturated; these oils may be wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passionflower oil or musk rose oil; or caprylic/capric acid triglycerides, for instance those sold by the company Stearineries Dubois or those sold under the names Miglyol 810®, 812®and 818® by the company Dynamit Nobel;

synthetic ethers containing from 10 to 40 carbon atoms;

linear or branched hydrocarbons of mineral or synthetic origin, such as petroleum jelly, polydecenes, hydrogenated polyisobutene such as Parleam, and squalane, and mixtures thereof;

synthetic esters, for instance oils of formula $R_1COOR_2$ in which $R_1$ represents a linear or branched fatty acid residue containing from 1 to 40 carbon atoms and $R_2$ represents a hydrocarbon-based chain, which may be branched, containing from 1 to 40 carbon atoms, on condition that $R_1+R_2 \geq 10$, for instance Purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, alcohol or polyalcohol octanoates, decanoates or ricinoleates, for instance propylene glycol dioctanoate; hydroxylated esters, for instance isostearyl lactate or diisostearyl malate; and pentaerythritol esters;

fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpenta-decanol;

higher fatty acids such as oleic acid, linoleic acid or linolenic acid; and mixtures thereof.

The non-volatile silicone oils that may be used in the composition according to the invention may be non-volatile polydimethylsiloxanes (PDMS), polydimethylsiloxanes comprising alkyl or alkoxy groups, which are pendent and/or at the end of a silicone chain, these groups each containing from 2 to 24 carbon atoms, phenyl silicones, for instance phenyl trimethicones, phenyl dimethicones, phenyltrimethylsiloxy-diphenylsiloxanes, diphenyl dimethicones, diphenylmethyl-diphenyltrisiloxanes and 2-phenylethyltrimethyl-siloxysilicates.

The fluoro oils that may be used in the invention are especially fluorosilicone oils, fluoro polyethers and fluorosilicones as described in document EP-A-847 752.

Thickening/Structuring Agent

The compositions according to the invention may be in anhydrous thickened form, for example in the form of a stick, especially when it is intended for application to the lips. They may be thickened with at least one thickener chosen from fatty-phase gelling agents, waxes, pasty fatty substances and fillers, and mixtures thereof.

Fatty-phase gelling agents that may be mentioned include optionally modified clays, for instance hectorites modified with a $C_{10}$ to $C_{22}$ fatty acid ammonium chloride, for instance hectorite modified with distearyldimethylammonium chloride; silica; partially or totally crosslinked elastomeric organopolysiloxanes of three-dimensional structure, for instance those sold under the names KSG6, KSG16 and KSG18 from Shin-Etsu, Trefil E-505C or Trefil E-506C from Dow Corning, Gransil SR-CYC, SR DMF 10, SR-DC556, SR 5CYC gel, SR DMF 10 gel and SR DC 556 gel from Grant Industries and SF 1204 and JK 113 from General Electric; galactomannans comprising from one to six and in particular from two to four hydroxyl groups per saccharide, substituted with a saturated or unsaturated alkyl chain, for instance guar gum alkylated with $C_1$ to $C_6$ and in particular $C_1$ to $C_3$ alkyl chains, and more particularly ethyl guar with a degree of substitution of 2 to 3, such as the product sold by the company Aqualon under the name N-Hance-AG; gums and especially silicone gums, for instance PDMSs with a viscosity >500 000 centistokes and/or a molecular weight of greater than or equal to 200 000 g/mol.

Silicone polyamides of the polyorganosiloxane type such as those described in documents U.S. Pat. Nos. 5,874,069, 5,919,441, 6,051,216 and 5,981,680 may also be used.

These silicone polymers may belong to the following two families:
polyorganosiloxanes comprising at least two groups capable of establishing hydrogen interactions, these two groups being located in the polymer chain, and/or
polyorganosiloxanes comprising at least two groups capable of establishing hydrogen interactions, these two groups being located on grafts or branches.

These gelling agents are used, for example, in concentrations of from 0.2% to 15% of the total weight of the composition.

The composition may also contain at least one wax.

For the purposes of the present invention, the term "wax" means a lipophilic fatty compound, which is solid at room temperature (25° C.), with a reversible solid/liquid change of state, having a melting point of greater than 30° C. that may be up to 200° C., a hardness of greater than 0.5 MPa, and having in the solid state an anisotropic crystal organization. By bringing the wax to its melting point, it is possible to make it miscible with oils and to form a microscopically homogeneous mixture, but on returning the temperature of the mixture to room temperature, recrystallization of the wax in the oils of the mixture is obtained.

The waxes that may be used in the invention are compounds that are solid at room temperature, which are intended to structure the composition in particular in stick form; they may be hydrocarbon-based waxes, fluoro waxes and/or silicone waxes and may be of plant, mineral, animal and/or synthetic origin. They may have a melting point of greater than 40° C. and better still greater than 45° C.

As waxes that may be used in the invention, mention may be made of those generally used in cosmetics: they may be of natural origin, for instance beeswax, carnauba wax, candelilla wax, ouricoury wax, Japan wax, cork fibre wax, sugarcane wax, rice wax, montan wax, paraffin, lignite wax or microcrystalline wax, ceresin or ozokerite, and hydrogenated oils, for instance jojoba oil; synthetic waxes, for instance the polyethylene waxes derived from the polymerization or copolymerization of ethylene and Fischer-Tropsch waxes, or alternatively fatty acid esters, for instance octacosanyl stearate, glycerides that are solid at 40° C. and better still at 45° C., silicone waxes, for instance alkyl or alkoxy dimethicones containing an alkyl or alkoxy chain of 10 to 45 carbon atoms, and poly(di)methylsiloxane esters that are solid at 40° C., the ester chain of which contains at least 10 carbon atoms; and mixtures thereof.

The compositions according to the invention may contain polyethylene wax with a weight-average molecular mass of between 300 and 700 and for instance equal to 500 g/mol.

As a guide, the wax may represent from 0.01% to 50%, from 2% to 40% and for example from 5% to 30% of the total weight of the composition.

The compositions may also contain at least one pasty compound.

For the purposes of the present invention, the term "pasty substance" is intended to denote a lipophilic fatty compound, with a reversible solid/liquid change of state, comprising at a temperature of 23° C. a liquid fraction and a solid fraction. The term "pasty substance" also means polyvinyl laurate.

The pasty compound may be chosen from the group consisting of:
  lanolin and its derivatives,
  polymeric or non-polymeric fluoro compounds,
  polymeric or non-polymeric silicone compounds,
  vinyl polymers, especially:
    olefin homopolymers
    olefin copolymers
    hydrogenated diene homopolymers and copolymers
    homopolymeric or copolymeric linear or branched oligomers of alkyl (meth)acrylates preferably containing a $C_8$-$C_{30}$ alkyl group
    homopolymeric and copolymeric oligomers of vinyl esters containing $C_8$-$C_{30}$ alkyl groups
    homopolymeric and copolymeric oligomers of vinyl ethers containing $C_8$-$C_{30}$ alkyl groups
    liposoluble polyethers resulting from polyetherification between one or more $C_2$-$C_{100}$ and preferably $C_2$-$C_{50}$ diols
    esters
and mixtures thereof.

Among the liposoluble polyethers that may be used, there are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made of copolymers such that the long-chain alkylene oxides are arranged in blocks with a mean molecular weight of from 1000 to 10 000, for example a polyoxyethylene/polydodecyl glycol block copolymer such as the ethers of dodecanediol (22 mol) and of polyethylene glycol (45 EO) sold under the brand name Elfacos ST9 by Akzo Nobel.

Among the pasty esters that may be used there are:
  esters of an oligomeric glycerol, such as diglycerol esters, such as condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially like those sold under the brand name Softisan 649 by the company Sasol,
  the arachidyl propionate sold under the brand name Waxenol 801 by Alzo,
  phytosterol esters,
  non-crosslinked polyesters resulting from the polycondensation between a linear or branched $C_4$-$C_{50}$ dicarboxylic or polycarboxylic acid and a $C_2$-$C_{50}$ diol or polyol, other than the polyester described above,
  aliphatic esters of an ester resulting from the esterification of an ester of an aliphatic hydroxycarboxylic acid with an aliphatic monocarboxylic acid; and mixtures thereof, for instance:
    the ester resulting from the esterification reaction of hydrogenated castor oil with isostearic acid in proportions of 1 to 1 (1/1) or hydrogenated castor oil monoisostearate,
    the ester resulting from the esterification reaction of hydrogenated castor oil with isostearic acid in proportions of 1 to 2 (1/2) or hydrogenated castor oil diisostearate,
    the ester resulting from the esterification reaction of hydrogenated castor oil with isostearic acid in proportions of 1 to 3 (1/3) or hydrogenated castor oil triisostearate,
    and mixtures thereof.

Among the pasty compounds of plant origin that may be chosen there is a mixture of soybean sterols and of oxyethylenated (5 EO) oxypropylenated (5 PO) pentaerythritol, sold under the reference Lanolide by the company Vevy.

The pasty compound may represent from 1% to 99%, from 1% to 60%, from 2% to 30% and even from 5% to 20% by weight of the composition.

As stated previously, the compositions according to the invention may also comprise one or more fillers, in a content ranging from 0.01% to 50% by weight and for instance ranging from 0.01% to 30% by weight relative to the total weight of the composition.

The term "fillers" should be understood as meaning white or colourless, mineral or synthetic particles of any form, which are insoluble in the medium of the composition irrespective of the temperature at which the composition is manufactured. These fillers serve especially to modify the rheology or the texture of the composition.

The fillers may be mineral or organic of any form, platelet-shaped, spherical or oblong. Mention may be made of talc, mica, silica, kaolin, polyamide (Nylon®) powders (Orgasol® from Atochem), poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) or of acrylic acid copolymers (Polytrape from the company Dow Corning) and silicone resin microbeads (for example Tospearls® from Toshiba), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and for instance from 12 to 18 carbon atoms, for example zinc stearate, magnesium stearate or lithium stearate, zinc laurate or magnesium myristate, and Polypore® L200 (Chemdal Corporation). Mention may also be made of silica-based fillers, for instance Aerosil 200, Aerosil 300; Sunsphere L-31 and Sunsphere H-31 sold by Asahi Glass; Chemicelen sold by Asahi Chemical; composites of silica and of titanium dioxide, for instance the TSG series sold by Nippon Sheet Glass. Finally, mention may be made of polyurethane powders, such as powders of crosslinked polyurethane comprising a copolymer, the said copolymer comprising trimethylol hexyllactone. It may be a polymer of hexamethylene diisocyanate/trimethylol hexyllactone. Such particles are especially commercially available, for example, under the name Plastic Powder D-400® or Plastic Powder D-800® from the company Toshiki.

Dyestuff

The compositions of the invention may comprise at least one dyestuff, which may be chosen from the group consisting of dyes, pigments and nacres, and mixtures thereof. This dyestuff may represent from 0.001% to 98%, from 0.5% to 85% and from 1% to 60% of the total weight of the composition.

For obvious reasons, these dyestuffs are used in the compositions according to the invention so as not to harm the effect more particularly desired according to the invention, and which may be directed towards affording a natural makeup effect.

For example, the dyestuffs may provide a colouring effect different from white. For instance, the dyestuffs are not transparent.

For a composition in paste or cast form such as lipsticks or body makeup products, from 0.5% to 50%, from 2% to 40% and from 5% to 30% of dyestuff is generally used relative to the total weight of the composition.

The dyes may be liposoluble dyes, although water-soluble dyes may be used. The liposoluble dyes are, for example, Sudan red, D & C Red 17, D & C Green 6, β-carotene, soybean oil, Sudan brown, D & C Yellow 11, D & C Violet 2, D & C Orange 5, quinoline yellow and annatto. They may represent from 0 to 20% and for example from 0.1% to 6% of the weight of the composition. The water-soluble dyes may be beetroot juice and methylene blue, and may represent from 0.1% to 6% by weight of the composition (if present).

The term "pigments" should be understood as meaning white or coloured, mineral or organic particles that are insoluble in the liquid fatty phase, which are intended to colour and/or opacify the composition. The term "nacres" should be understood as meaning iridescent particles, for example produced by certain molluscs in their shell, or else synthesized.

The pigments may be present in the composition in a proportion of from 0.05% to 30% and for example in a proportion of from 2% to 20% of the weight of the final composition. As mineral pigments that may be used in the invention, mention may be made of titanium oxide, zirconium oxide or cerium oxide, and also zinc oxide, iron oxide or chromium oxide and ferric blue. Among the organic pigments that may be used in the invention, mention may be made of carbon black, and barium, strontium, calcium (D & C Red No. 7) and aluminium lakes.

The nacres may be present in the composition in a proportion of from 0.001% to 20% and for example in a proportion of about from 1% to 15% of the total weight of the composition. Among the nacres that may be used in the invention, mention may be made of mica coated with titanium oxide, with iron oxide, with natural pigment or with bismuth oxychloride, such as coloured titanium mica.

The compositions may also contain goniochromatic pigments, for example multilayer interference pigments, and/or reflective pigments. These two types of pigment are described in patent application FR 02/09246.

Additional Components

According to one embodiment, the compositions under consideration according to the invention may be combined in the compositions according to the invention with other active agents capable of contributing towards producing the desired effect, i.e. a healthy complexion effect on the skin and/or the lips, or a fleshy effect on the lips.

This active agent may, for example, promote blood capillary circulation in the contacted keratin material.

It may thus be a compound chosen from the group consisting of:
agents that promote the production of nitrogen monoxide;
antihypertensive agents; in particular potassium channel openers;
phosphodiesterase inhibitors;
flavonoids or flavoglycosides;
glucosides;
plant extracts with vasodilatory properties;
vasodilatory peptides that are not NO donors;
other vasodilatory agents; and
temperature regulators.

The compositions according to the invention may also contain ingredients commonly used in cosmetics, such as vitamins, trace elements, softeners, sequestrants, fragrances, basifying or acidifying agents, preserving agents, sunscreens, surfactants, film-forming polymers, antioxidants and propellants, or mixtures thereof.

Needless to say, a person skilled in the art will take care to select this or these optional additional compound(s), and/or the amount thereof, such that the properties of the corresponding composition according to the invention are not, or are not substantially, adversely affected by the envisaged addition.

The compositions according to the invention may be manufactured via the known processes generally used in cosmetics or dermatology. They may be obtained by heating the various constituents to the melting point of the highest-melting waxes, followed by pouring the molten mixture into a mould (dish or finger stall). They may also be obtained by extrusion, as described in patent application EP-A-667 146.

The composition of the invention may be in solid, pasty or more or less fluid liquid form. It may be a gloss or a soft paste for caring for or making up the lips.

The invention is illustrated in greater detail in the examples that follow. The percentages are given on a weight basis.

EXAMPLES

Gloss Formulations

EXAMPLE 1

| Components | Concentration (mass %) |
|---|---|
| Polybutene MW: 920 | 29.95 |
| Polybutene MW: 1290 | 34.00 |
| Isononyl isononanoate | 2.89 |
| 2-Octyldodecanol | 9.39 |
| Tridecyl trimellitate | 13.14 |
| Glyceryl caprylate[1] | 5.00 |
| Hydrophobic fumed silica, surface-treated with dimethylsilane | 5.00 |
| Fragrance | 0.5 |
| Sodium saccharinate | 0.12 |

[1]Capmul 708G-Abitec

| Components | Concentration (mass %) | | |
|---|---|---|---|
| | Example 2 | Example 3 | Example 4 |
| Isononyl isononanoate | 4 | 4 | 4 |
| Glyceryl caprylate/caprate[2] | 1.5 | 0 | 1.5 |
| 2-Octyldodecanol | 10 | 10 | 10 |
| Mixture of isobutyl and N-butyl p-hydroxy-benzoate (40/30/30) | 0.4 | 0.4 | 0.4 |
| Polybutene (MW: 2060) | 4 | 4 | 4 |
| Caprylyl glycol[3] | 0 | 1 | 0.5 |
| Polybutene (MW: 1290) | 30 | 30 | 30 |
| Polybutene (MW: 920) | 29.75 | 30.25 | 29.25 |
| Pentaerythrityl tetraisostearate (qs) | 20.35 | 20.35 | 20.35 |
| Total: | 100 | 100 | 100 |

[2]Capmul MCM from Abitec
[3]Dermosoft Octiol from Straetmans

After applying each of the above glosses to the lips, swelling of the lips is observed, affording an appreciable fleshy or pouty effect that is perceptible to the user.

The invention claimed is:

1. A cosmetic method comprising at least the step of applying to skin and/or lips at least one glycol with a $C_7$-$C_{12}$-hydrocarbon-based chain and a hydroxylated ester resulting from the esterification of polyol and of $C_4$-$C_{16}$ carboxylic acid(s), in a composition for caring for and/or making up the skin and/or the lips, as an agent for reinforcing a natural flesh tint of the skin and/or of the lips and/or the natural volume of the lips, wherein the hydroxylated ester is present in the composition in a content ranging from 0.2% to 5% by weight relative to a total weight of the composition.

2. The cosmetic method according to claim 1, wherein said agent is applied to give the skin of the face a healthy complexion effect.

3. The cosmetic method according to claim 1, wherein said agent is applied to homogenize and/or clarify the complexion and/or reduce the hazy complexion effect.

4. The cosmetic method according to claim 1, wherein said agent is applied to increase the size and/or volume of the lips and/or model them and/or make them smoother.

5. The cosmetic method according to claim 1, wherein said agent is applied to stimulate natural coloration of the lips.

6. The cosmetic method according to claim 1, wherein said ester is a hydroxylated monoester, a hydroxylated diester or a mixture thereof.

7. The cosmetic method according to claim 1, wherein the ester is of $C_{10}$-$C_{20}$ and contains at least one fatty chain.

8. The cosmetic method according to claim 1, wherein said ester bears at least two free OH function(s) on its alcohol residue.

9. The cosmetic method according to claim 1, wherein the polyol is a saturated or unsaturated, linear or branched $C_2$-$C_{15}$ hydrocarbon-based derivative containing at least two free hydroxyl functions.

10. The cosmetic method according to claim 1, wherein the polyol is a $C_2$-$C_8$ hydrocarbon-based derivative.

11. The cosmetic method according to claim 1, wherein the polyol is chosen from propylene glycol and glycerol.

12. The cosmetic method according to claim 1, wherein the acid is a saturated or unsaturated $C_7$-$C_{10}$ monocarboxylic hydrocarbon-based derivative.

13. The cosmetic method according to claim 1, wherein the acid is chosen from heptanoic acid, caprylic acid and capric acid.

14. The cosmetic method according to claim 1, wherein said agent is chosen from monoglyceryl and/or diglyceryl caprylate, monoglyceryl and/or diglyceryl heptanoate, propylene glycol caprylate and propylene glycol heptanoate, and mixtures thereof.

15. The cosmetic method according to claim 1, wherein said agent comprises at least monoglyceryl caprylate.

16. The cosmetic method according to claim 1, wherein the glycol has a $C_7$-$C_{10}$ hydrocarbon-based chain.

17. The cosmetic method according to claim 16, wherein the glycol has a $C_8$-$C_{10}$ hydrocarbon-based chain.

18. The cosmetic method according to claim 1, wherein the glycol is caprylyl glycol.

19. The cosmetic method according to claim 1, wherein the composition is suitable for topical application.

20. The cosmetic method according to claim 1, wherein the composition is in the form of a care base, a care cream, a makeup base, a tinted cream, a foundation, a lipstick, a liquid gloss, a lip paste, a lip contour pencil, a lip balm or a lip varnish.

21. A cosmetic composition for caring for and/or making up the skin and/or the lips, containing, in a physiologically acceptable medium, less than 5% by weight of water and at least one glycol with a $C_7$-$C_{12}$ hydrocarbon-based chain and a hydroxylated ester of polyol and of $C_4$-$C_{16}$ carboxylic acid(s),
wherein said polyol is selected from the group consisting of glycerol, glycols, and derivatives thereof; and
wherein the hydroxylated ester is present in the cosmetic composition in a content ranging from 0.2% to 5% by weight relative to a total weight of the cosmetic composition.

22. The cosmetic composition according to claim 21, comprising less than 1% by weight of water.

23. The cosmetic composition according to claim 21, said composition being anhydrous.

24. A cosmetic composition for caring for and/or making up the skin and/or the lips, containing, in a physiologically acceptable medium, at least:
one dyestuff, and
at least one glycol with a $C_7$-$C_{12}$ hydrocarbon-based chain and a hydroxylated ester of polyol and of $C_4$-$C_{16}$ carboxylic acid(s),
wherein said polyol is selected from the group consisting of glycerol, glycols, and derivatives thereof; and
wherein the hydroxylated ester is present in the cosmetic composition in a content ranging from 0.2% to 5% by weight relative to a total weight of the cosmetic composition.

25. The cosmetic composition according to claim 21, containing at least one non-aqueous solvent phase.

26. The cosmetic composition according to claim 24, containing at least one non-aqueous solvent phase.

27. The cosmetic composition according to claim 21, comprising at least one thickener chosen from the group consisting of waxes and pasty fatty substances.

28. The cosmetic composition according to claim 24, comprising at least one thickener chosen from the group consisting of waxes and pasty fatty substances.

29. The cosmetic composition according to claim 21, containing at least one dyestuff chosen from the group consisting of pigments, nacres and dyes.

30. The cosmetic composition according to claim 24, containing at least one dyestuff chosen from the group consisting of pigments, nacres and dyes.

31. The cosmetic composition according to claim 21, containing at least one filler.

32. The cosmetic composition according to claim 24, containing at least one filler.

33. The cosmetic composition according to claim 21, wherein said composition is in the form of a makeup product for the lips or the skin.

34. The cosmetic composition according to claim 24, wherein said composition is in the form of a makeup product for the lips or the skin.

35. The cosmetic composition according to claim 34, wherein said composition is in the form of a lip makeup product.

36. A cosmetic method for making up the skin and/or the lips which is applied to give a healthy complexion effect, comprising the step of applying to skin and/or lips a cosmetic composition for caring for and/or making up the skin and/or the lips, containing, in a physiologically acceptable medium, less than 5% by weight of water and at least one glycol with a $C_7$-C hydrocarbon-based chain and a hydroxylated ester of polyol and of $C_4$-$C_{16}$ carboxylic acid(s), wherein said polyol is selected from the group consisting of glycerol, glycols, and derivatives thereof; and wherein the hydroxylated ester is present in the cosmetic composition in a content ranging from 0.2% to 5% by weight relative to a total weight of the cosmetic composition.

37. A cosmetic method for making up the skin and/or the lips which is applied to give a healthy complexion effect, comprising the step of applying to skin and/or lips a cosmetic composition for caring for and/or making up the skin and/or the lips, containing, in a physiologically acceptable medium, at least:

one dyestuff, and at least one glycol with a $C_7$-$C_{12}$ hydrocarbon-based chain and a hydroxylated ester of polyol and of $C_4$-$C_{16}$ carboxylic acid(s), wherein said polyol is selected from the group consisting of glycerol, glycols, and derivatives thereof; and wherein the hydroxylated ester is present in the cosmetic composition in a content ranging from 0.2% to 5% by weight relative to a total weight of the cosmetic composition.

38. A cosmetic method for making up the lips, comprising the application to the lips of a cosmetic composition for caring for and/or making up the skin and/or the lips, containing, in a physiologically acceptable medium, less than 5% by weight of water and at least one glycol with a $C_7$-$C_{12}$ hydrocarbon-based chain and a hydroxylated ester of polyol and of $C_4$-$C_{16}$ carboxylic acid(s), wherein said polyol is selected from the group consisting of glycerol, glycols, and derivatives thereof; and wherein the hydroxylated ester is present in the cosmetic composition in a content ranging from 0.2% to 5% by weight relative to a total weight of the cosmetic composition.

39. A cosmetic method for making up the lips, comprising the application to the lips of a cosmetic composition for caring for and/or making up the skin and/or the lips, containing, in a physiologically acceptable medium, at least:

one dyestuff, and at least one glycol with a $C_7$-$C_{12}$ hydrocarbon-based chain and a hydroxylated ester of polyol and of $C_4$-$C_{16}$ carboxylic acid(s), wherein said polyol is selected from the group consisting of glycerol, glycols, and derivatives thereof; and wherein the hydroxylated ester is present in the cosmetic composition in a content ranging from 0.2% to 5% by weight relative to a total weight of the cosmetic composition.

40. The cosmetic composition according to claim 21, containing from 0.05% to 20% by weight of said glycol relative to the total weight of the composition.

41. The cosmetic composition according to claim 24, containing from 0.05% to 20% by weight of said glycol relative to the total weight of the composition.

* * * * *